United States Patent [19]

Geria

[11] Patent Number: 5,019,033
[45] Date of Patent: May 28, 1991

[54] OINTMENT APPLICATOR AND METHOD OF USING

[75] Inventor: Navin M. Geria, Warren, N.J.

[73] Assignee: Warner-Lambert Company, Morris Plains, N.J.

[21] Appl. No.: 452,916

[22] Filed: Dec. 18, 1989

[51] Int. Cl.$^5$ ............................................. A61H 15/00
[52] U.S. Cl. ...................................... 604/2; 604/310; 401/261; 401/266; 401/183
[58] Field of Search ...................... 604/2, 3, 305, 306, 604/309, 310, 289, 290, 294, 295, 301; 401/132, 133, 196, 198, 199, 202, 203, 183–185, 28

[56] References Cited

U.S. PATENT DOCUMENTS

| | | | |
|---|---|---|---|
| 339,652 | 4/1886 | Horton | 401/183 |
| 344,949 | 7/1886 | Dick | 604/309 |
| 507,860 | 10/1893 | Vint | 604/309 |
| 588,091 | 8/1897 | Sanche | 604/305 |
| 590,405 | 9/1897 | Sieghortner | 604/2 |
| 677,861 | 9/1900 | Booth | 604/2 |
| 886,984 | 5/1908 | Jopling | 401/183 |
| 1,705,256 | 3/1929 | Krusi | 604/2 |
| 1,939,612 | 12/1933 | Rose | 604/310 |
| 3,054,403 | 9/1962 | Baker | 604/2 |
| 3,228,057 | 1/1966 | Parrish | 604/2 |
| 3,876,314 | 4/1975 | Nehring | 604/2 |
| 3,891,331 | 6/1975 | Avery | 604/2 |
| 4,148,318 | 4/1979 | Meyer | 604/3 |
| 4,183,684 | 1/1980 | Avery, Jr. | 604/3 |
| 4,329,990 | 5/1982 | Sneider | 604/2 |

FOREIGN PATENT DOCUMENTS 0577563  6/1933  Fed. Rep. of Germany ...... 604/289

Primary Examiner—John D. Yasko
Assistant Examiner—Anthony Gutowski
Attorney, Agent, or Firm—Charles A. Gaglia, Jr.

[57] ABSTRACT

A disposable hollow bulb-shaped applicator has an ointment-permeable soft mesh membrane which covers the bulbous end of the applicator. Resilient walls surround and interconnect both ends of the applicator, and form a chamber for holding ointment therebetween. The applicator has a necked end opposite to the bulbous end which may be attached to a container of ointment. The ointment chamber of the applicator may be filled with ointment by pressurizing the container (e.g. by squeezing) to force ointment from the container into the applicator. A plug is inserted into the necked end of the applicator to prevent the flow of ointment out of the applicator through the necked end. The filled applicator is squeezed to force ointment through the soft mesh membrane and onto the surface which is to be treated by the ointment. The applicator may be discarded after use.

12 Claims, 2 Drawing Sheets

OINTMENT APPLICATOR AND METHOD OF USING

FIELD OF THE INVENTION

The present invention relates generally to ointment applicators. More specifically, this invention relates to disposable applicators which are filled from a squeeze tube of ointment. The present invention is particularly, though not exclusively, useful for applying ointment uniformly onto uneven, tender areas of flesh, such as hemorrhoidal tissue.

BACKGROUND OF THE INVENTION

Applicators for applying ointment to treat skin surfaces of the human body are well known in the art and have a wide range of uses. One example of a treatment ointment applicator is a pile pipe, which is often used in the treatment of hemorrhoidal tissue. Pile pipes are small cones formed with holes in the sides of the cone through which ointment is exuded onto the affected tissue when the pile pipe is positioned next to the hemorrhoidal tissue. Although sufficient for their intended use, pile pipes have certain drawbacks. For example, a recent United States Government monograph, which was published by the Food and Drug Administration to provide guidance in the area of rectal ointment treatment, indicates that pile pipes should not be used for applying ointment to hemorrhoidal tissue if they contain local anesthetic. This is because pile pipes are inserted internally into the body. Since the human rectum has no nerve endings within approximately three to four inches of the anus, the FDA monograph concluded there is no rationale for internally applying local anesthetics over the last three to four inches of the anal canal. Therefore, the FDA monograph recommends that in view of the factors discussed above, hemorrhoidal treatment ointments which contain local anesthetics should be applied only externally to the anus.

Existing external ointment applicators, however, possess certain disadvantages when compared to internal ointment applicators, such as the pile pipe described above. The chief disadvantage of many external ointment applicators is that they are incapable of uniformly applying ointment to the often irregularly-shaped hemorrhoidal tissue, without imposing undue discomfort on the patient. The present invention recognizes the need for external, uniform application of ointment containing local anesthetic upon hemorrhoidal tissue, without imposing discomfort on the patient.

Accordingly, the present invention provides an external ointment applicator which can uniformly apply ointment to an irregularly shaped surface, such as hemorrhoidal tissue. Further, the present invention provides an external ointment applicator which can apply ointment to a tender area of skin, such as hemorrhoidal tissue, in a manner which minimizes patient discomfort. Additionally, the present invention provides an external ointment applicator which is hygienic, easy to use, disposable, and cost effective to manufacture.

SUMMARY OF THE INVENTION

A disposable hollow bulb-shaped applicator has continuous walls which diverge from the applicator's narrow, or necked end, to the applicator's wider, or bulbous, end. The applicator's walls are formed of an elastic material, to permit the walls to partially collapse. By being callapsible, the walls provide means to expel ointment from the applicator by squeezing the walls, as well as provide a cushioning effect when the applicator contacts the tissue on which the ointment is to be applied. An ointment-permeable soft mesh membrane is connected to the edge of the walls to cover and define the bulbous end of the applicator. This soft mesh membrane is preferably composed of a non-fibrous elastic material which gently surrounds and uniformly applies ointment to the potentially uneven surfaces which are to be treated. The applicator may be filled with ointment by attaching an ointment source, such as a squeeze tube, to the applicator's necked end and forcing ointment into the applicator. A plug, such as a rubber or neoprine plug, is then pushed into the applicator's necked end to hold the ointment in the applicator. The filled applicator is then positioned against the surface to be treated and squeezed to force ointment through the soft mesh membrane and onto the surface to be treated. The applicator may be discarded after use.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
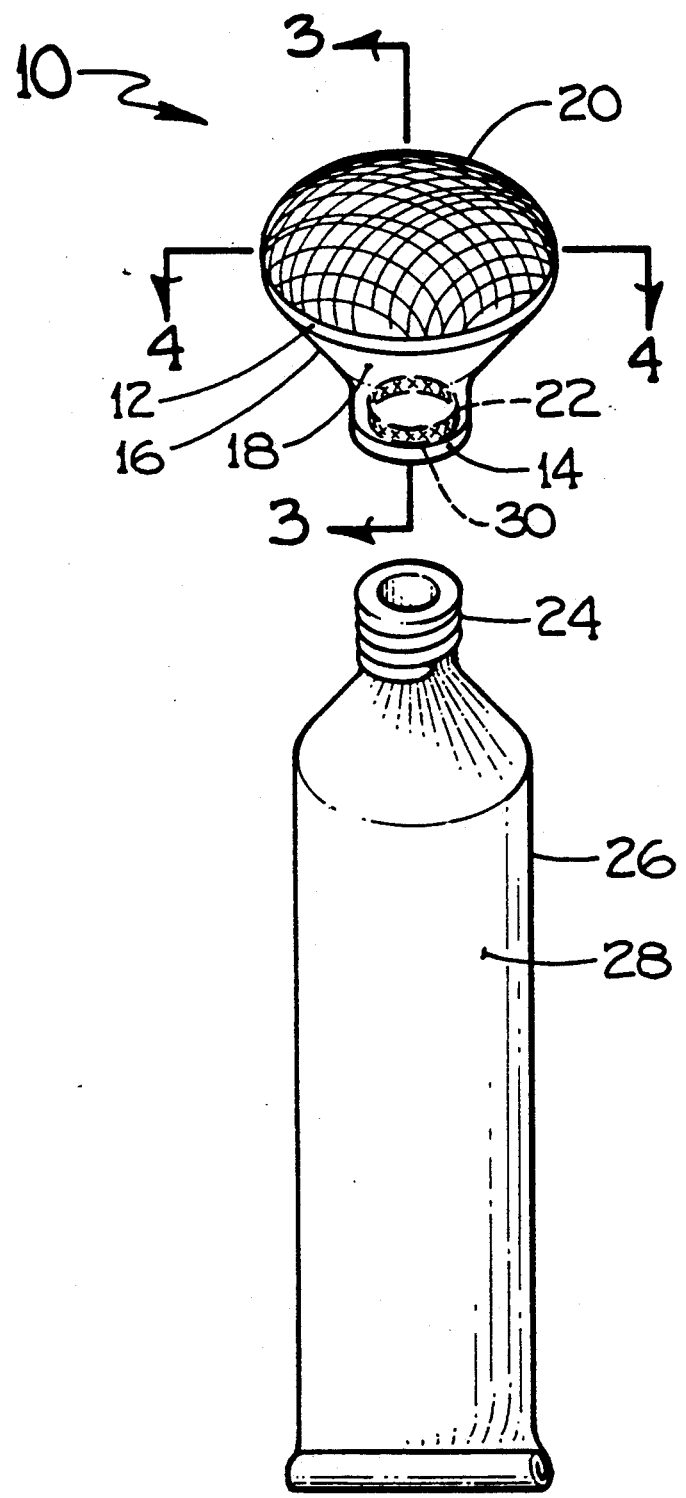
FIG. 1 is a perspective view of the external applicator device showing it in position for attachment to a tube of ointment for filling the device with ointment.

Referring initially to FIG. 1, it may be seen that an external applicator device, generally designated 10, comprises an elastic applicator ring 12, an elastic neck ring 14, and a divergent elastic resilient wall 16 disposed therebetween to form a substantially conical ointment chamber 18. Extending over and attached to applicator ring 12 is an ointment permeable mesh cover 20. As shown in phantom in FIG. 1, one embodiment of external applicator 10 envisions knurls 22 formed on the inner circumference of neck ring 14, for threadable engagement with threads 24 of ointment tube 26.

In the embodiment shown, external applicator 10 may be filled with ointment 28 by engaging knurls 22 with threads 24, and then squeezing tube 26 to expel ointment 28 out of tube 26 through opening 30 of neck ring 14 and into ointment chamber 18. It is to be understood, however, that external applicator 10 may be filled with ointment using any suitable filling means. Indeed, external applicator 10 may even be pre-filled with ointment during the manufacturing process.

Figure 2:
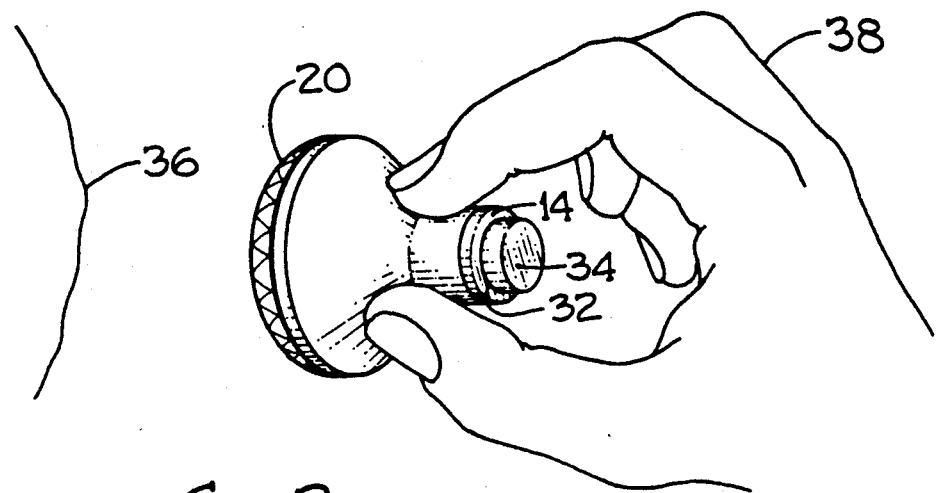
FIG. 2 is a view showing the external applicator device being applied to an uneven tissue surface.
Figure 3:
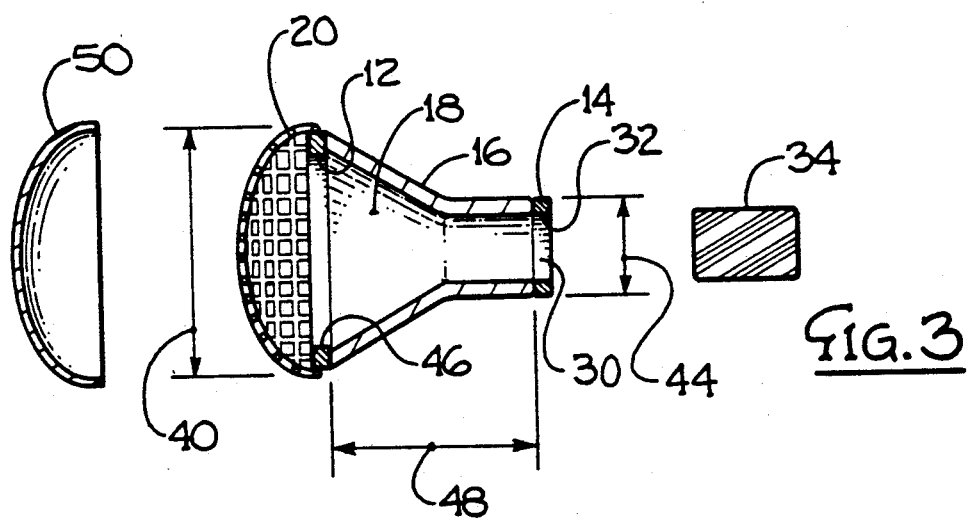
FIG. 3 is an exploded cross-sectional view of the external applicator device as seen along the line 3-3 in FIG. 1.

As further shown by referring to FIGS. 2 and 3, after external applicator 10 is filled with ointment, opening 30, defined by inner periphery 32 of neck ring 14, may be covered by any means well known in the art, such as by the insertion of a plug 34 into opening 30. When opening 30 is so covered, external applicator 10 may be placed against a tissue surface 36 and then squeezed by operator 38 to force ointment through meshed cover 20 and onto surface 36. As will be appreciated by the skilled artisan, applicator 10 can also be squeezed to force ointment through meshed cover 20 before applicator 10 is placed in contact with surface 36. In either case, after treatment, external applicator 10 may be disposed in any suitable receptacle.

Figure 4:
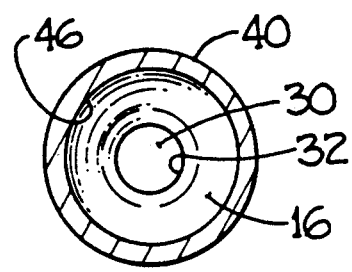
FIG. 4 is a view of the external applicator device as seen along the line 4—4 in FIG. 1.

The details of external applicator 10 may be best described by cross reference to FIGS. 3 and 4. In FIG. 3, it may be seen that meshed cover 20 is attached around a periphery 40 of applicator ring 12 to cover an opening 46 which is defined by periphery 40. Meshed cover 20 is attached to periphery 40 by any means well known in the art, such as by solvent bonding or gluing. As shown in FIG. 3, meshed cover 20 is flaccidly connected to periphery 40 such that meshed cover 20 forms a substantially bulb-shaped cushioning surface when ointment chamber 18 is filled with ointment. When so constructed and attached, meshed cover 20 is able to conform to the potentially irregular surface to be treated. Importantly, with this construction meshed cover 20 is able to effect a cushioned and comfortable, yet uniform application of ointment over the entire area of the external tissue surface 36 to be treated. As can be appreciated by the skilled artisan, meshed cover 20 may be made of any soft, non-fibrous, ointmentporous material such as cotton, silk, nylon, rayon, etc. It is important, however, that the material used for meshed cover 20 be able to contain ointment 28 in ointment chamber 18 for a reasonable length of time, e.g. sufficient time to fill the applicator 10 and carry it into position against tissue surface 36. Additionally, the material of meshed cover 20, like the materials used in other components of external applicator 10, should be chemically compatible with the ointment in chamber 18. Likewise, the materials of external applicator 10 should remain relatively chemically inert when exposed to sunlight.

FIG. 3 also shows divergent wall 16 attached to and interconnecting applicator ring 12 and neck ring 14. The wall 16 forms the hollow ointment chamber 18, which contains the treatment ointment, and is composed of a collapsible yet resilient material, such as thin plastic, to provide a cushioning effect by partially collapsing when external applicator 10 is applied to the surface to be treated. Further, wall 16 is flexible in order that it may be squeezed to exude ointment 18 through meshed cover 20. After applicator 10 is withdrawn from the treated surface, wall 16, being resilient, recovers its divergent shape shown in FIG. 3. As the skilled artisan will appreciate, in order to enable wall 16 to provide the cushioning effect described above, ointment chamber 18 should initially be only partly filled with ointment. In the preferred embodiment, the conical volume described by chamber 18 is half-filled with ointment prior to use.

As further shown in FIG. 3, the degree of divergence of walls 16 is partially defined by the diameters 42 and 44 of applicator ring 12 and neck ring 14, respectively. As can be appreciated, the distance 48 between rings 12 and 14, and the diameters 42 and 44 of ring 12 and 14, respectively, define a divergence for wall 16 which is conducive to a collapsing of walls 16 during ointment application. Subsequently, this divergence for wall 16 allows recovery of its shape, as described above. Because rings 12 and 14 are substantially circular, wall 16 form an ointment chamber 18 which is substantially a hollow cone.

By cross referencing FIGS. 3 and 4, it will be seen that a plug 34 may be inserted into opening 30 of neck ring 14 to establish an interference fit between plug 34 and periphery 32. It is to be understood that while the embodiment of external applicator 10 shown in FIG. 3 contemplates the use of a rubber or neoprine plug 34 to impede the passage of ointment through opening 30, any suitable means may be used to prevent ointment in chamber 18 from flowing out of chamber 18 through opening 30.

A plastic laminate cover 50 is also shown in FIG. 3, laminate cover 50 being removably attached to meshed cover 20 by any means well known in the art. It will be understood that laminate cover 50 is to be removed from meshed cover 20 prior to using applicator 10. It will be further understood that covering meshed cover 20 with laminate cover 50 provides a hygienic barrier for meshed cover 20 prior to using applicator 10.

OPERATION

The operation of external applicator 10 is best seen by cross-referencing FIGS. 1 and 2. External applicator 10 is initially charged with ointment 28 by threadably engaging knurls 22 of neck ring 14 with threads 24 of ointment tube 26. Ointment tube 26 is then squeezed to force ointment 28 through the opening 30, and into ointment chamber 18. After thus filling approximately fifty percent (50%) of the volume of ointment chamber 18 with ointment 28, applicator 10 is threadably disengaged from tube 26. Plug 34 is then inserted into opening 30 to prevent ointment 28 from exiting ointment chamber 18 through opening 30. Laminate cover 50 is then removed from meshed cover 20, and meshed cover 20 is positioned against the surface 36 to be treated, as shown in FIG. 2. Applicator 10 is subsequently squeezed by operator 38 to force ointment 28 through meshed cover 20 and onto surface 36 to treat surface 36.

While the particular external applicator device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A disposable hollow ointment applicator which comprises:
    a first periphery forming a first opening;
    a second periphery forming a second opening, said second opening having a diameter smaller than said first opening;
    a continuous elastic wall attached to and circumscribing said peripheries and disposed therebetween to form a substantially cone shaped hollow chamber for holding ointment therein; and
    an ointment permeable membrane disposed around said first periphery to cover said first opening and hold ointment in said chamber until said ointment is forced through said membrane in response to closing said second opening squeezing said wall.

2. A disposable hollow ointment applicator as recited in claim 1, further comprising:
    a source of ointment; and
    means to attach said applicator to said source for filling said chamber with said ointment.

3. A disposable hollow ointment applicator as recited in claim 1 wherein said membrane comprises a meshed, non-fibrous material.

4. A disposable hollow ointment applicator as recited in claim 1 further comprising a plug for insertion into said second opening to establish an interference fit between said plug and said second periphery.

5. A disposable hollow ointment applicator as recited in claim 1 wherein said membrane is covered with a removable nonporous laminate layer.

6. A bulb-shaped ointment applicator which comprises:
   a first periphery defining a first substantially circular opening therethrough;
   elastic walls diverging from said first opening to an expanded, substantially circular distal opening forming a unitary, funnel-shaped device; and
   an ointment-permeable membrane disposed around said distal opening to confine ointment within said device until said ointment is forced through said membrane is response to closing said second opening and squeezing said walls.

7. A bulb-shaped ointment applicator as recited in claim 6 further comprising:
   a source of ointment; and
   means to attach said applicator to said source for filling said chamber with ointment.

8. A bulb-shaped ointment applicator as recited in claim 6 wherein said ointment-permeable means comprises a meshed, non-fibrous membrane.

9. A bulb-shaped ointment applicator as recited in claim 6 further comprising an ointment-impermeable plug for insertion by an interference fit into said first opening.

10. A bulb-shaped ointment applicator as recited in claim 6 wherein said ointment permeable means is covered with a removable non-porous layer disposed over said means opposite to said distal opening.

11. A bulb-shaped ointment applicator as recited in claim 6 wherein said walls comprise a resilient elastic material.

12. A method for applying ointment to an erose surface comprising the steps of:
   (A) Disposing resilient walls between a first periphery defining a first opening and a second periphery defining a second opening, said second opening having a larger area in cross-section then said first opening, said walls forming a chamber;
   (B) Covering said second opening with an ointment permeable membrane;
   (C) Transferring said ointment from an ointment source into said chamber through said first opening;
   (D) Covering said first opening with an ointment impermeable means;
   (E) Positioning said permeable membrane adjacent said surface; and
   (F) Squeezing said walls to expel said ointment from said chamber through said membrane and onto said surface.

* * * * *